United States Patent
Tseng et al.

(10) Patent No.: US 6,872,946 B2
(45) Date of Patent: Mar. 29, 2005

(54) METHOD AND SAMPLING DEVICE FOR DETECTION OF LOW LEVELS OF A PROPERTY/QUALITY TRAIT PRESENT IN AN INHOMOGENEOUSLY DISTRIBUTED SAMPLE SUBSTRATE

(75) Inventors: Ching-Hui Tseng, West Chester, OH (US); Kangming Ma, Mason, OH (US); Nan Wang, West Chester, OH (US); Daniel McFadden, Cincinnati, OH (US)

(73) Assignee: Cognis Corporation, Ambler, PA (US)

( * ) Notice: Subject to any disclaimer, the term of this patent is extended or adjusted under 35 U.S.C. 154(b) by 220 days.

(21) Appl. No.: 10/366,166

(22) Filed: Feb. 13, 2003

(65) Prior Publication Data

US 2003/0168600 A1 Sep. 11, 2003

Related U.S. Application Data

(60) Provisional application No. 60/361,245, filed on Mar. 1, 2002.

(51) Int. Cl.$^7$ ............................................... G01N 21/35
(52) U.S. Cl. ................................................. 250/339.07
(58) Field of Search ...................... 250/339.07; 356/244

(56) References Cited

U.S. PATENT DOCUMENTS

| | | |
|---|---|---|
| 4,968,938 A | 11/1990 | Pines et al. |
| 5,171,995 A | 12/1992 | Gast et al. |
| 5,184,191 A | 2/1993 | Krishnan |
| 5,408,512 A | 4/1995 | Kuwabara et al. |
| 5,886,525 A | 3/1999 | Yesinowski et al. |
| 5,936,244 A | 8/1999 | Yajima et al. |
| 6,483,583 B1 * | 11/2002 | Wright et al. ............... 356/326 |

* cited by examiner

Primary Examiner—David Porta
Assistant Examiner—Marcus Taningco
(74) Attorney, Agent, or Firm—Aaron R. Ettelman

(57) ABSTRACT

A process for detecting low levels of a predetermined quality trait present in an inhomogeneously distributed particulate substrate involving the steps of: (a) providing a particulate substrate to be analyzed; (b) providing a spectrometer with an electromagnetic detector capable of performing spectroscopic measurements with electromagnetic radiation; (c) providing a rotatable sample holder having a transparent area through which electromagnetic radiation may pass; (d) providing a tumbling member located within the rotatable sample holder for tumbling the particulate substrate contained therein; (e) introducing the particulate substrate into the rotatable sample holder; (f) simultaneously rotating and tumbling the particulate substrate contained within the rotatable sample holder; and (g) activating the spectrometer, thereby illuminating the particulate substrate contained within the rotatable sample holder with electromagnetic radiation.

20 Claims, 1 Drawing Sheet

METHOD AND SAMPLING DEVICE FOR DETECTION OF LOW LEVELS OF A PROPERTY/QUALITY TRAIT PRESENT IN AN INHOMOGENEOUSLY DISTRIBUTED SAMPLE SUBSTRATE

CROSS-REFERENCE TO RELATED APPLICATIONS

This application claims the benefit of copending provisional application Ser. No. 60/361,245 filed on Mar. 1, 2002.

STATEMENT REGARDING FEDERALLY SPONSORED RESEARCH OR DEVELOPMENT

Not applicable.

BACKGROUND OF THE INVENTION

One common phenomenon which continues to plague grain farmers relates to the infestation of whole grain seeds with a disease such as, for example, *Fusarium*. This in turn causes a small percentage of grain kernels to contain a high level of a mycotoxin that is inhomogeneously distributed within random samples of the grain.

Deoxynivalenol (hereinafter referred to as "DON" or "Vomitoxin") is one of the toxic 12,13-epoxytrichothecenes produced by various species of *Fusarium*, especially *F. graminearum*. The presence of DON typically occurs in barley, wheat and other feed grains that are grown under certain climatic conditions. As a result, the quality of beer can be adversely affected when malting barley containing significant concentrations of DON is used. Moreover, illnesses have been observed in livestock that have consumed feed grains containing high levels of DON concentration. Consequently, wheat and barley lots are oftentimes discounted in value when sold on the open market, as soon as it is detected that DON concentrations present in those lots exceed certain predetermined levels. Hence, due to the significant economic issue involved, the accuracy and precision of DON measurements sampled from grain lots is of great financial concern.

Currently, levels of DON are typically measured in the marketing channels with commercially available test kits, based on enzyme linked immunosorbent assay (ELISA) technology. This method requires the use of a series of procedures/steps including grinding, cleaning and extraction. Due to the toxicity of DON, only qualified technicians are capable of running these tests. Although this method of analysis for DON is currently the grain industry standard, its tedious nature make it difficult, if not impossible, to perform quick and easy analyses out in the field. Clearly, therefore, there is a significant need in the grain industry for alternative methods of DON analysis which enable accurate analyses to be performed, in the field, quickly, easily and in a nondestructive manner.

Near infrared analysis has been used successfully in the grain industry for protein and moisture content analyses. There have been reports regarding the use of NIR and FTIR to perform DON analyses. However, in those cases FTIR was not used by itself, but rather as a detector in combination with gas chromatography. As for the use of NIR, reports have indicated the inability to detect DON at low ppm levels, which are commonplace, due to the inhomogeneous distribution of the infected kernels.

BRIEF SUMMARY OF THE INVENTION

The present invention is directed to a process for detecting low levels of a predetermined quality trait present in an inhomogeneously distributed particulate substrate involving the steps of: (a) providing a particulate substrate to be analyzed; (b) providing a spectrometer with an electromagnetic detector capable of performing spectroscopic measurements with electromagnetic radiation; (c) providing a rotatable sample holder having a transparent area through which electromagnetic radiation may pass; (d) providing a tumbling member located within the rotatable sample holder for tumbling the particulate substrate contained therein; (e) introducing the particulate substrate into the rotatable sample holder; (f) simultaneously rotating and tumbling the particulate substrate contained within the rotatable sample holder; and (g) activating the spectrometer, thereby illuminating the particulate substrate contained within the rotatable sample holder with electromagnetic radiation.

The present invention is also directed to an apparatus for detecting low levels of quality traits present in inhomogeneously distributed particle substrates comprising: (a) a spectrometer with an electromagnetic detector capable of performing spectroscopic measurements with electromagnetic radiation; (b) a rotatable sample holder having a transparent area through which electromagnetic radiation may pass; and (c) a tumbling member located within the rotatable sample holder for tumbling the particulate substrate contained therein.

DETAILED DESCRIPTION OF THE INVENTION

Figure 1:
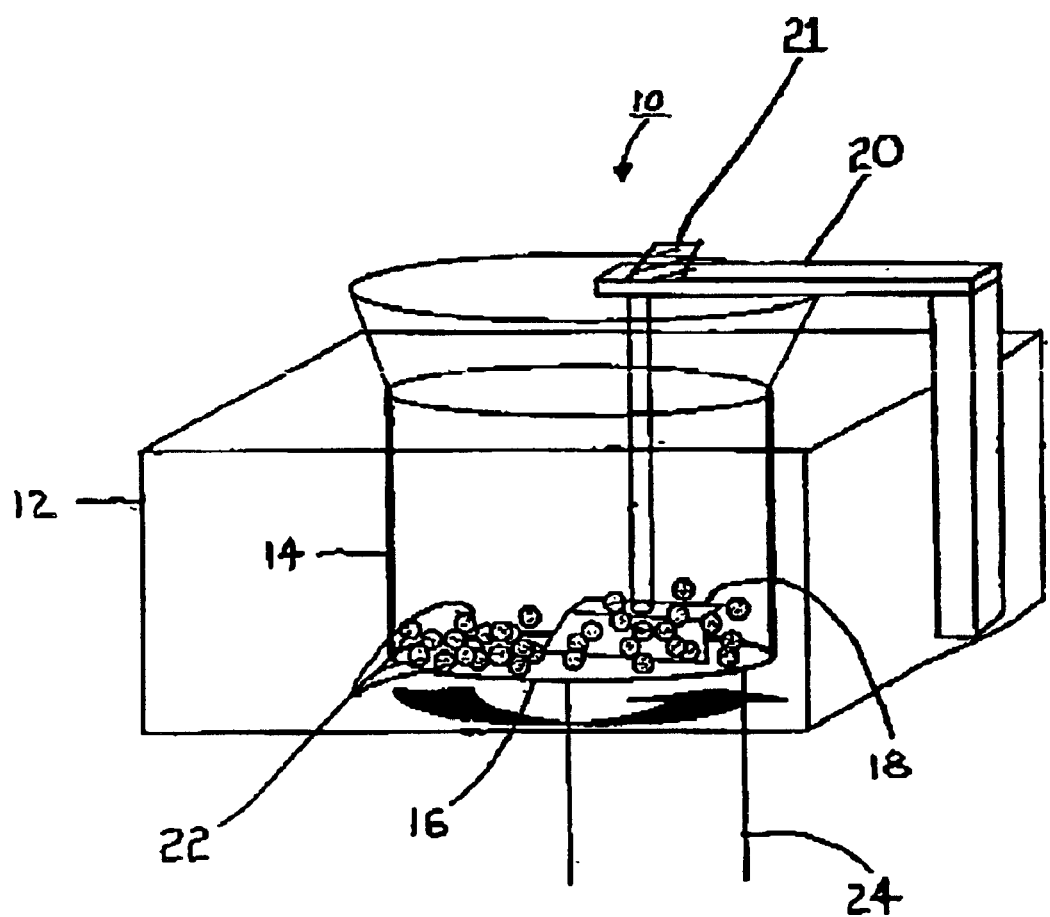
FIG. 1 is a side elevation view of a preferred embodiment of the present invention Sampling Device.

Referring to the drawings, wherein like numerals indicate like elements throughout, there is shown in FIG. 1 a sampling device presently preferred and referred to generally by reference numeral 10. The sampling device 10 comprises a spectrometer 12 having a rotatable sample holder 14 present therein. The rotatable sample holder 14 has a transparent wall 16 capable of allowing electromagnetic radiation generated by the spectrometer 12 to pass through the rotatable sample holder 14.

The spectrometer 12 must have means for both retaining and rotating the rotatable sample holder 14 within the spectrometer 12. The speed of rotation should be variable so as to provide efficient mixing for thorough analysis of each and every particulate substrate being analyzed.

A tumbling member 18 is removably disposed within the rotatable sample holder 14. A handle member 20, connected to the tumbling member 18 is provided in order to insert and remove the tumbling member from inside the rotatable sample holder 14. The handle member 20 is provided with a weight member 21, attached thereto, in order to stabilize the tumbling member 18 during use. It should be noted, however, that the means by which the tumbling member 18 is disposed and stabilized within the rotatable sample holder 14 is not critical. Any suitable means may be employed without departing from the spirit of the invention.

In a particularly preferred embodiment of the present invention, as is best seen in FIG. 1, the rotatable sample holder 14 is in the form of a cylindrical cup. It should be noted, however, that the rotatable sample holder 14 may take on any shape suitable for retaining both a particulate substrate 22 and tumbling member 18 therein, without departing from the spirit of the invention.

It is also preferred that a glass base member, which is transparent in a predetermined wavelength region of the electromagnetic radiation, serves as the transparent wall 16 of the rotatable sample holder 14. The area of the transparent wall 16 is preferably about 20 mm in diameter. The precise shape, density, diameter, etc. of the transparent wall 16 will depend on the type of measurements being taken and the type of electromagnetic radiation being employed.

Moreover, it should also be noted that the transparent wall 16 may be made of any suitable material capable of allowing electromagnetic radiation of a predetermined wavelength to pass therethrough, without departing from the spirit of the invention. A more thorough description concerning this aspect of the invention can be found in U.S. Pat. No. 5,171,995, the entire contents of which is hereby incorporated by reference.

The rotatable sample holder 14 is preferably made from metal or antistatic plastic in order to facilitate easy cleaning of any residue present therein after each measurement. Similarly, the tumbling member 18 is also preferably made from metal or anti-static plastic. The width of the bottom edge of the tumbling member 18 should be greater than the diameter of the electromagnetic radiation beam 24, and preferably about the same as the inner radius of the rotatable sample holder 14. This enables all of the particulate substrate 22 to be tumbled after each measurement, and most of the particulate substrate 22 located at the bottom of the rotatable sample holder 14 to be tumbled after one complete rotation. It should be noted, however, that the width should not be so large as to allow the tumbling member 18 to be flipped out. The bottom edge of the tumbling member 18 should be symmetrically even and sharp enough to allow any dust present on the transparent wall 16 to be cleaned during rotation. The angle of the tumbling member 18 has to be such that it is positioned in a direction opposite to the direction in which the particulate substrate 22 is moving in order to ensure that the handle member 20 does not get pushed upwardly within the rotatable sample holder 14 while the particulate substrate 22 is moving.

In a particularly preferred embodiment of the present invention, the spectrometer is a portable IR spectrophotometer having a rotating sample cup for holding sample grains to be analyzed such as one commercially available from Bruker Corporation, under the tradename MATRIX-F®.

In operation, the tumbling member 18 is first disposed within the rotatable sample holder 14 using handle member 20 which lowers the tumbling member 18 into the rotatable sample holder 14. A particulate substrate 22 to be analyzed, is then deposited into the rotatable sample holder 14. The spectrometer 12 is then actuated causing the rotatable sample holder 14 to rotate. As the rotatable sample holder 14 rotates, it causes the particulate substrate 22 to come into contact with the tumbling member 18, thereby continuously tumbling the particulate substrate 22 within the rotatable sample holder 14.

Since certain types of properties/quality traits commonly present in solid substrates are oftentimes distributed inhomogeneously in and around each individual substrate particle such as, for example, a grain kernel, it is imperative that the maximum amount of collectable information relating to each individual kernel be obtained. Based on the ability to vary the rotating speed of the rotatable sample holder 14, the tumbling member 18 is capable of thoroughly mixing grain kernels contained therein, automatically, throughout the entire scan period, thereby maximizing the amount of information, i.e., properties/qualities possessed by the grain kernels, which are present at levels as low as ppm, and lower. The combination of the tumbling member 18 coupled with the ability to variably control the rotation of the rotatable sample holder 14, in conjunction with the large illumination area of the transparent wall 16, and extended scan time, allows the spectrometer to collect maximum information from individual kernels.

The data obtained using the above-disclosed device can also be used to generate calibration models for use in combination with the above-described invention. For example, sample lots of barley and wheat may be analyzed, as is, without the need for any sample preparation involving various chemical procedures as is currently the industry standard. Once a requisite of analyses are complete, a calibration model can be developed in order to enable sample substrate to be tested in the field, at remote locations, for the presence of properties/quality traits present in low levels within inhomogeneous samples.

The present invention will be better understood from the examples which follow, all of which are intended for illustrative purposes and are not meant to unduly limit the scope of the invention in any way.

EXAMPLES

Two DON analysis calibration models for wheat and barley were separately generated with an IR spectrophotometer using predetermined settings on the scan time and sample size. 100 grams of each sample were placed into the rotating sample cup of the sampling device, and scanned five times with 256 scans at a resolution of 16 cm$^{-1}$. The average spectrum of these five spectra was then used to build a calibration model the partial least squares (PLS) method.

Levels of DON in the range of 0 to 15 ppm were successfully detected using the present invention, with better accuracy than conventionally-used primary chemical methods.

The sampling device of the present invention is capable of analyzing various properties/quality traits which are inhomogeneously located at low levels throughout a sample substrate. Examples thereof include other types of mycotoxins/fungus, free fatty acids present on the surface of rice sample, chlorophyll, fiber contents, minerals, polymer materials, pharmaceutical tablets, etc.

What is claimed is:

1. A sampling device for detecting low levels of predetermined quality traits present in inhomogeneously distributed particulate substrates comprising:

(a) a spectrometer capable of generating a beam of electromagnetic radiation, the spectrometer having an electromagnetic detector capable of performing spectroscopic measurements with electromagnetic radiation;

(b) a rotatable platform located within the spectrometer;

(c) a rotatable sample holder resting on the rotatable platform, the rotatable sample holder being capable of simultaneously holding and rotating a particulate substrate to be analyzed, and having a transparent wall through which electromagnetic radiation may pass; and (d) a tumbling member removably disposed within the rotatable sample holder for continuously tumbling a particulate substrate contained therein during rotation.

2. The sampling device of claim 1 wherein the spectrometer is an infrared spectrometer.

3. The sampling device of claim 1 wherein the rotatable sample holder has a cylindrical cup shape.

4. The sampling device of claim 1 wherein the transparent wall is made of glass.

5. The sampling device of claim 1 wherein the transparent wall has a diameter of 20 mm.

6. The sampling device of claim 1 wherein the rotatable platform further comprises means for varying its speed of rotation.

7. The sampling device of claim 1 further comprising a handle member for removably disposing the tumbling member within the rotatable sample holder.

8. The sampling device of claim 1 wherein a bottom edge of the tumbling member has a width greater than a diameter of the electromagnetic radiation beam.

9. The sampling device of claim 1 wherein a bottom edge of the tumbling member has a width equal to an inner radius of the rotatable sample holder.

10. The sampling device of claim 1 wherein the rotatable sample holder is made of a material selected from the group consisting of metal and anti-static plastic.

11. A process for detecting low levels of predetermined quality traits present in inhomogeneously distributed sample particulate substrates comprising:

(a) providing a particulate substrate;
   (b) providing a spectrometer capable of generating a beam of electromagnetic radiation, the spectrometer having an electromagnetic detector capable of performing spectroscopic measurements with electromagnetic radiation;
   (c) providing a rotatable platform located within the spectrometer;
   (d) providing a rotatable sample holder resting on the rotatable platform, the rotatable sample holder being capable of simultaneously holding and rotating a particulate substrate to be analyzed, and having a transparent wall through which electromagnetic radiation may pass;
   (e) providing a tumbling member removably disposed within the rotatable sample holder for continuously tumbling the particulate substrate contained therein during rotation;
   (f) disposing the tumbling member within the rotatable sample holder;
   (g) depositing particulate substrate into the rotatable sample holder; and
   (h) actuating the spectrometer, whereby the rotatable sample holder resting on the rotatable platform rotates, causing the particulate substrate to continuously tumble by coming into contact with the tumbling member, at the same time a beam of electromagnetic radiation passes through the transparent wall of the rotatable sample holder and onto the particulate substrate contained therein resulting in spectroscopic measurements being taken by the electromagnetic detector.

12. The process of claim 11 wherein the spectrometer is an infrared spectrometer.

13. The process of claim 11 wherein the rotatable sample holder has a cylindrical cup shape.

14. The process of claim 11 wherein the transparent wall is made of glass.

15. The process of claim 11 wherein the transparent wall has a diameter of 20 mm.

16. The process of claim 11 wherein the rotatable platform further comprises means for varying its speed of rotation.

17. The process of claim 11 further comprising a handle member for removably disposing the tumbling member within the rotatable sample holder.

18. The process of claim 11 wherein a bottom edge of the tumbling member has a width greater than a diameter of the electromagnetic radiation beam.

19. The process of claim 11 wherein a bottom edge of the tumbling member has a width equal to an inner radius of the rotatable sample holder.

20. The process of claim 11 wherein the rotatable sample holder is made of a material selected from the group consisting of metal and anti-static plastic.

\* \* \* \* \*